United States Patent [19]

Menon

[11] Patent Number: 5,061,068

[45] Date of Patent: Oct. 29, 1991

[54] PROCESS FOR DETECTION OF SUB-MICRON PARTICULATE CONTAMINATION ON A BARE (PLANAR) SUBSTRATE

[75] Inventor: Venugopal B. Menon, Austin, Tex.

[73] Assignee: Research Triangle Institute, Research Triangle Park, N.C.

[21] Appl. No.: 482,887

[22] Filed: Feb. 22, 1990

[51] Int. Cl.$^5$ ............................................. G01B 9/02
[52] U.S. Cl. ................................... 356/345; 356/357; 356/237
[58] Field of Search ............... 356/345, 355, 357, 237, 356/239, 336, 362, 38

[56] References Cited

U.S. PATENT DOCUMENTS 3,767,306 10/1973 Mast et al. .......................... 356/336

*Primary Examiner*—Samuel Turner
*Attorney, Agent, or Firm*—Oblon, Spivak, McClelland, Maier & Neustadt

[57] ABSTRACT

Particular contamination below about 0.3 microns in average diameter on an IC wafer substrate is detected by forming a film of a volatile liquid on the wafer's surface and observing interference patterns formed by particles during the evaporation process. These interference patterns magnify the "effective" particle size many times, making detection through an optical microscope possible.

9 Claims, No Drawings

PROCESS FOR DETECTION OF SUB-MICRON PARTICULATE CONTAMINATION ON A BARE (PLANAR) SUBSTRATE

BACKGROUND OF THE INVENTION

1. Field of the Invention

The invention pertains to the detection of sub-micron particles, particularly particles below about 0.3 microns in average diameter, present on the surface of a bare (planar) substrate as contaminates. Particular attention is paid to the detection of particles on substrates for integrated circuit manufacture.

2. Background of the Prior Art

Recent developments in integrated circuit technology have seen a rapid shift to increased density and decreased spacing of circuit elements in integrated circuits. All indications are that this trend will increase, and perhaps accelerate, in the next few years. Particulate contaminates present on the surface of a substrate on which a IC is built are potentially capable of causing fatal defects to the IC. Accordingly, there is a need to detect, and thereby eliminate sub-micron sized particles from an IC wafer surface. Particles below 0.1 micron in size, about 0.05 microns, present on the wafer surface can greatly reduce yield, at the current level of semiconductor technology. As density values increase, the diameter of the particle likely to cause a fatal defect will shrink.

Currently available technology to detect the presence of small particles rests principally with laser surface scanners. Although a wide variety are available, they are generally incapable of resolving particles smaller than about 0.2–0.3 microns. While scanning electron microscopes can resolve particles much smaller than this, they scan extremely smaller areas, at any given time. The scanning process for a relatively small wafer, i.e., 3–4 inches, extends over several hours. This is simply not consistent with commercial demands. Accordingly, it remains a pressing object of the industry to provide a swift, reliable method for detecting particles smaller than about 0.3 microns average diameter on the surface of a wafer or other IC substrate, which technique requires a relatively short time.

SUMMARY OF THE INVENTION

A non-destructive method for the detection of particles below about 0.3 microns in size, and the sizing and counting thereof, requires the formation of a film of a low-boiling point liquid on the substrate surface. The temperature of the substrate is controlled, so as to induce slow evaporation of the film. The surface tension phenomena cause those portions of the film surrounding sub-micron particles to evaporate more slowly than the remaining portion of the film. As light passes through the film (e.g., using the reflected light of an optical microscope) circular interference patterns are formed around each particle because of the differential in evaporation. These interference patterns are clearly visible, making the "effective" diameter of the particle many times larger than its actual size. The diameter of the interference ring, and its time of appearance during the evaporation process allows one to determine the size of the particle. Microscopic observations are recorded on videotape and/or converted to digital information for ease of detection.

DETAILED DESCRIPTION OF THE INVENTION

The non-destructive detection process of the invention begins with the formation of a low-boiling point liquid film on the surface of the substrate. Virtually any low-boiling point film is acceptable, as the interference pattern created is a physical, rather than a chemical phenomena. Because of their wide availability, low toxicity and easy handling, the alcohols are preferred liquids for use in the invention. Particularly preferred liquids, given their boiling point are ethanol and isopropanol, as the use of these alcohols can easily be adapted to a conventional optical microscope, with a cooling stage, which allows easy control of the substrate temperature and speed of evaporation.

The thickness of the film formed is not critical. If too thick a film is formed, the evaporation process will simply take longer until interference patterns are produced. The thinner the film formed, the better.

As noted, the process is non-destructive, and positive results allow the IC wafer inspected to be subsequently used in manufacture. Accordingly, every effort should be taken to make sure that the liquid film is not, itself, a source of particulate contamination. Although most alcohols can be obtained in relatively particle-free condition, it is easier to purify and filter gases. Accordingly, in a preferred embodiment, the film is formed by a condensation of vapor of the liquid on the surface of the substrate. This can easily be done, for example, by a distillation tube, which is caused to recondense over the substrate itself.

Once the film is formed, microscopic observation of the substrate, through light passing through the film is initiated. Conveniently, the light may be reflected light from a conventional optical microscope, although other adaptations will occur to those of skill in the art. The light is essential because, as the film evaporates, the area around the particle contaminates evaporates more slowly than the remainder of the film. This produces interference rings or interference patterns as the light passes through the film. These interference patterns occur but briefly, and real time processing may be difficult or impossible. Accordingly, the view through the microscope is recorded on videotape. This videotape may either be scanned directly or converted to digital information by currently available software. Such digital information may be easily processed by a microcomputer, microprocessor, etc., to both count particles, and size them.

As noted, the interference ring formed corresponds to the size of the particles. Additionally, the time of formation of the interference pattern is indicative of the size of the particle responsible. Thus, larger particles are detected first, with smaller particles being made evident subsequent in the process. The process may be standardized and calibrated by the deposition, on a sample substrate, of a known quantity of particles of known diameter, i.e., particles previously obtained through a sizing process. More sophisticated calibration can be obtained by depositing 2 or 3 classes of particles (in terms of size) on a single wafer. The size differential can be confirmed by the fact that the interference ring formed is of different diameter, and by the fact that different interference patterns are observed at different times during the evaporation process.

Laboratory runs using particles of known size have demonstrated detection of particles as small as 0.08 microns in average diameter, or smaller. It is believed, with optimization of equipment, such as improved microscopic observation, and frame by frame video analysis, coupled with possible conversion to digital information, that particles as small as 0.01 microns can be detected through this process.

Obviously numerous modification and variations of the present invention are possible in light of the above teachings. It is therefore to be understood that within the scope of appended claims, the invention may be practiced otherwise than as specifically described herein.

What is claimed is:

1. A process for the detection of sub-micron particles on the surface of a substrate, comprising:

forming a film of a low-boiling liquid alcohol on said substrate surface, elevating the temperature of said surface so as to cause slow evaporation of said film, shining light through said film and observing said light as said film evaporates to detect interference patterns formed in said film, wherein said interference patterns correspond to a particle on said surface, wherein interference patterns which occur early in the evaporation process correspond to particles larger than those indicated by interference patterns occurring later in the evaporation process.

2. The process of claim 1, wherein said alcohol is a C1-6 alcohol.

3. The process of claim 2, wherein said alcohol is ethanol, isopropanol or a mixture thereof.

4. The process of claim 1, wherein said observation is recorded visually and employed to monitor the evaporation process.

5. The process of claim 1, wherein said observation is recorded in digital form, and the number, time and size of each interference pattern is determined by computing means.

6. The process of claim 1, wherein said substrate is comprised of silicon.

7. The process of claim 1, wherein said particles are less than 0.3 microns in average diameter.

8. The process of claim 1, wherein said film is formed by condensation of vapor of said liquid on said surface.

9. The process claim 8, wherein said vapor is purified prior to film formation to remove particulates therefrom.

* * * * *